United States Patent [19]
Lohse et al.

[11] 3,981,898
[45] Sept. 21, 1976

[54] POLYSILOXANES CONTAINING HYDROXYL GROUPS

[75] Inventors: Friedrich Lohse, Oberwil, Switzerland; Kurt Munk, Wyhlen, Germany; Heinz Rembold, Arlesheim, Switzerland

[73] Assignee: Ciba-Geigy Corporation, Ardsley, N.Y.

[22] Filed: Mar. 17, 1975

[21] Appl. No.: 558,996

[30] Foreign Application Priority Data
Mar. 25, 1974 Switzerland.................... 4107/74

[52] U.S. Cl........................................ 260/448.8 R
[51] Int. Cl.$^2$............................................ C07F 7/18
[58] Field of Search .......................... 260/448.8 R

[56] References Cited
UNITED STATES PATENTS

| | | | |
|---|---|---|---|
| 3,293,211 | 12/1966 | Krimm et al. | 260/448.8 R X |
| 3,317,460 | 2/1967 | Clark et al. | 260/448.8 R X |
| 3,576,028 | 4/1971 | Fish | 260/448.8 R |

FOREIGN PATENTS OR APPLICATIONS

| | | | |
|---|---|---|---|
| 341,816 | 6/1972 | U.S.S.R. | 260/448.8 R |

*Primary Examiner*—Paul F. Shaver
*Attorney, Agent, or Firm*—Luther A. R. Hall

[57] ABSTRACT

Polysiloxanes containing hydroxyl groups are manufactured by reacting polysiloxanes, which have been (so-called) advanced with polyols and which contain alkoxy groups, with aliphatic or cycloaliphatic diols in the presence of a catalyst at elevated temperatures. The new polysiloxanols can be used as modifiers for organic resins such as urethane resins or epoxide resins, and give flexible, hydrophobic plastics having valuable mechanical properties.

5 Claims, No Drawings

POLYSILOXANES CONTAINING HYDROXYL GROUPS

The present invention relates to new polysiloxanes containing hydroxyl groups, processes for their manufacture and the use of the new polysiloxanols for the manufacture and modification of organic resins.

Plastics modified with siloxane compounds are known. Polysiloxanes possessing hydroxyl end groups have also already been proposed for the purpose of modifying synthetic resins. British Pat. Specification No. 880,022 describes a process for the manufacture of polyoxyalkylene-polisiloxanediol block copolymers by reaction of polyoxyalkylene glycols of a particular chain length with polysiloxanes having two alkoxy end groups. Where these polysiloxanediol block copolymers are water-insoluble compounds, they are used as plasticisers for rubbers. However, when used as modifiers for synthetic resins they suffer from the disadvantage that they do not impart hydrophobic properties to the modified resin.

German Auslegeschrift 1,618,836 proposes trisiloxanols, of which the hydroxyl groups are bonded directly to the Si atoms, as modifiers for organic resin, such as polyester, urethane and epoxide resins. However, these siloxanols suffer from the disadvantage that their processing with organic resins presents difficulties so that they are not very suitable for use as modifiers.

It has now been found that reaction of polysiloxanes containing hydroxyl, alkoxy and acyloxy end groups with polyols and diols in certain retios gives new polysiloxanols which do not suffer from the abovementioned disadvantages, can easily be manufactured in accordance with the invention and impart advantageous properties to the modified resin, in particular in respect of very low water absorption, and at the same time render them very hydrophobic.

The subject of the present invention are new polysiloxane compounds containing hydroxyl groups, of the formula I

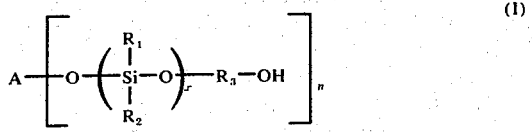

wherein A denotes the radical, obtained by removal of n hydroxyl groups, of a n-hydric aliphatic, cycloaliphatic-aliphatic, aromatic-aliphatic or N-heterocyclic-aliphatic polyol, $R_1$ and $R_2$ are identical or different and each denote a methyl, ethyl, propyl or phenyl group, and $R_1$ and/or $R_2$ can denote different substituents within the siloxane chain, $R_3$ denotes an alkylene radical with 2–8 C atoms, an optionally alkyl-substituted alkylene radical with 2–8 C atoms in the alkylene chain, which chain can be interrupted by a

group, or a cycloaliphatic-aliphatic, heterocyclic-aliphatic or aromatic-aliphatic radical, n denotes a number from 2 to 4 and x denotes a number from 2 to 30.

Preferably, in the formula I, A denotes the radical, obtained by removal of 2 or 3 hydroxyl groups, of a respectively 2-hydric or 3-hydric aliphatic or cycloaliphatic-aliphatic polyol with 2–15 C atoms in the molecule, $R_1$ and $R_2$ each denote a methyl, ethyl, propyl or phenyl group, and $R_1$ and $R_2$ on the same Si atom denote identical substituents and within the siloxane chain denote different substituents, $R_3$ denotes an alkylene radical with 2–6 C atoms, an alkylene radical, substituted by lower alkyl groups, with 2–6 C atoms in the alkylene chain, or a cycloaliphatic-aliphatic radical, n denotes the number 2 to 3 and x denotes a number from 2 to 20.

In particular, the present invention relates to polysiloxane compounds, containing hydroxyl groups, of the formula II

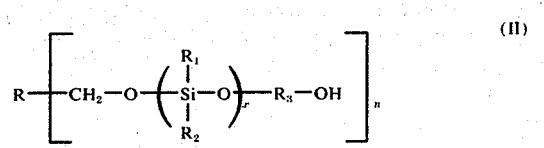

wherein R denotes the radical, obtained by removal of n hydroxymethyl groups, of a n-hydric aliphatic, cycloaliphatic-aliphatic aromatic-aliphatic or N-heterocyclic-aliphatic polyol, $R_1$ and $R_2$ are identical or different and each denote a methyl, ethyl, propyl or phenyl group, and $R_1$ and/or $R_2$ can denote different substituents within the siloxane chain, $R_3$ denotes an alkylene radical with 2–8 C atoms, an optionally alkyl-substituted alkylene radical with 2–8 C atoms in the alkylene chain, which chain can be interrupted by a

group, or a cylcoaliphatic-aliphatic, heterocyclic-aliphatic or aromatic-aliphatic radical, n denotes a number from 2 to 4 and x denotes a number from 2 to 30.

In particular, in the formula II, R denotes the radical, obtained by removal of 2 or 3 hydroxymethyl groups, of a respectively 2-hydric or 3-hydric aliphatic or cycloaliphatic-aliphatic polyol with 2–10 C atoms in the molecule, $R_1$ and $R_2$ each denote a methyl, ethyl, propyl or phenyl group, and $R_1$ and $R_2$ on the same Si atom denote identical substituents and within the siloxane chain denote different substituents, $R_3$ denotes an alkylene radical with 2–6 C atoms, an alkylene radical, substituted by lower alkyl groups, with 2–6 C atoms in the alkylene chain or a cycloaliphatic-aliphatic radical, n denotes the number 2 or 3 and x denotes a number from 2 to 20.

Compounds of the formula II which are of particular interest are those wherein, in the linear polysiloxane chain, dimethylsiloxane units alternate with dipropylsiloxane or diphenylsiloxane units and $R_3$ denotes the lower alkyl-substituted alkylene radical, with 2 or 3 C atoms, preferably 3 C atoms, in the alkylene chain, obtained by removal of the primary and secondary hydroxyl group.

The new polysiloxane compounds, containing hydroxyl groups, of the formula I are manufactured by reacting 1 mol of a polyol of the formula III

wherein n denotes a number from 2 to 4 and A denotes the radical, obtained by removal of n hydroxyl groups, of a n-hydric aliphatic, cycloaliphatic-aliphatic, aromatic-aliphatic or N-heterocyclic-aliphatic polyol, with n mols of a polysiloxane of the formula IV

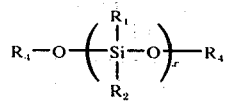 (IV)

wherein $R_1$ and $R_2$ are identical or different and each denote a methyl, ethyl, propyl or phenyl group, and $R_1$ and $R_2$ within the plysiloxane chain can denote different substituents, the radicals $R_4$ each denote a hydrogen atom, an alkyl group or an acyl group and x represents a number from 2 to 30, to give compounds of the formula V

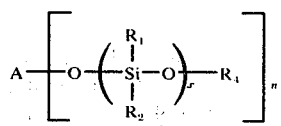 (V)

and, in a second stage, reacting these with n mols of a diol of the formula VI $$HO-R_3-OH \qquad (VI)$$

wherein $R_3$ denotes an optionally alkyl-substituted alkylene radical with 2–8 C atoms in the alkylene chain, which chain can be interrupted by a

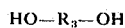

group, or a cycloaliphatic-aliphatic heterocyclic-aliphatic or aromatic-aliphatic radical.

In particular, the starting materials used in this process are compounds of the formula IV, wherein the radicals $R_4$ denote lower alkyl groups and x denotes a number from 2 to 20.

Preferably, the invention relates to a process for the manufacture of polysiloxane compounds, containing hydroxyl groups, of the formula II

 (II)

wherein R denotes the radical, obtained by removal of n hydroxymethyl groups, of a n-hydric aliphatic, cycloaliphatic-aliphatic, aromatic-aliphatic or N-heterocyclic-aliphatic polyol. $R_1$ and $R_2$ are identical or different and each denote a methyl, ethyl, propyl or phenyl group, and $R_1$ and $R_2$ can denote different substituents within the siloxane chain, $R_3$ denotes an optionally alkyl-substituted alkylene radical with 2–8 C atoms in the alkylene chain, which chain can be interrupted by a

group, or a cycloaliphatic-aliphatic, heterocyclic-aliphatic or aromatic-aliphatic radical, n denotes a number from 2 to 4 and x denotes a number from 2 to 30, characterised in that, in the first stage, 1 mol of a polyol of the formula (IIIa)

$$R+CH_2-OH)_n \qquad (IIIa)$$

wherein R and n have the same meaning as in the formula II, is reacted with n mols of a polysiloxane of the formula (IV)

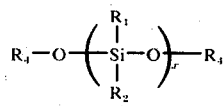 (IV)

wherein $R_1$, $R_2$ and x have the same meaning as in the formula II, and the radicals $R_4$ each denote a hydrogen atom, an alkyl group or an acyl group, to give compounds of the formula VII

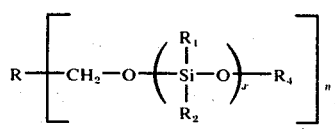 (VII)

and, in the second stage, these are reacted with n mols of a diol of the formula VI $$HO-R_3-OH \qquad (VI)$$

wherein $R_3$ has the same meaning as in the formula II, to give compounds of the formula II.

The preferred starting materials used in the process for the manufacture of compounds of the formula II are diprimary or tri-primary aliphatic or cycloaliphatic-aliphatic polyols of the formula IIIa which contain 2–10 C atoms in the molecule, and these are reacted, in the first stage, with polysiloxanes of the formula IV, wherein $R_1$ and $R_2$ each denote a methyl, ethyl, propyl or phenyl group, and $R_1$ and $R_2$ on the same Si atom denote identical substituents and within the siloxane chain denote different substituents, in particular with dimethylsiloxane units alternating with dipropylsiloxane or diphenylsiloxane units in the linear polysiloxane chain, the radicals $R_4$ denote lower alkyl groups, especially methyl groups, and x denotes a number from 2 to 20, and the resulting reaction product is reacted, in the second stage, with diols of the formula VI, wherein $R_3$ denotes an alkylene radical with 2–6 C atoms, an alkylene radical, substituted by lower alkyl groups, with 2–6 C atoms in the alkylene chain, or a cycloaliphatic-aliphatic radical, especially a lower alkyl-substituted alkylene radical with 2 or 3 C atoms in the alkylene chain.

In a preferred embodiment of the process for the manufacture of the polysiloxanols according to the invention, of the formula II, 1 mol of a n-hydric polyol of the formula IIIa is reacted, in a single stage, with n mols of a polysiloxane of the formula IV and n mols of a diol of the formula VI which possesses a primary and secondary hydroxyl group in the molecule.

The reaction of the polysiloxanes, having hydroxyl, alkoxy and acyloxy end groups, of the formula IV, with the polyols of the formula III or IIIa and the glycols of the formula VI can be carried out according to known processes, in a single stage or in two stages.

To manufacture pure polysiloxanols of the formula I, it is advisable to use the two-stage process wherein, in the first stage, 1 mol of a n-hydric polyol of the formula III, preferably a di-primary or tri-primary alcohol, is reacted with n mols or a polysiloxane of the formula IV and the resulting reaction product is then reacted, in the second stage, with the diol of the formula VI. As a rule, isolation of the intermediate product obtained from the polyol of the formula III and the polysiloxane of the formula IV is unnecessary.

Some polysiloxanols which correspond to the formula II can also be manufactured in a single stage from the compounds of the formulae IIIa, IV and VI, by using a di-, tri- or tetra-primary polyol of the formula IIIa and, as the diol of the formula VI, a diol which contains both a primary and a secondary hydroxyl group in the molecule, or if the diols of the formula III or IIIa and VI are identical di-primary diols.

The reactions can be carried out in a known manner by mixing the polysiloxanes, having hydroxyl, alkoxy or acyloxy end groups, of the formula IV, with the polyols of the formula III, if appropriate in the presence of the diols of the formula VI, in the stated ratio and at elevated temperatures, and reacting the mixture in the temperature range of about 100 to 250°C, preferably 150° to 220°C, until the theoretical amount of water, alcohol or monocarboxylic acid liberated in the reaction is obtained. The end of the reaction can also be determined with the aid of a sample which has been cooled to room temperature. When the reaction has been completed, phase separation no longer occurs in a cooled sample.

The course of the reaction can also be followed analytically be means of proton-magnetic resonance spectroscopy. As the reactions take place, for example, the signals of the SiOCH$_3$ protons at δ3.2–3.6 (100 Mc, recorded in CDCl$_3$) disappear completely and are replaced by the signals of the SiOCH$_2$ protons at δ3.6–4.0 (100 Mc, recorded in CDCl$_3$).

As a rule, the presence of a catalyst is superfluous in this process. However, basic, acid or neutral catalysts can be used to accelerate the reaction. The catalysts used are preferably organic titanium compounds, such as tetrabutyl titanate or tetraisopropyl titanate, quaternary ammonium salts, such as tetramethylammonium chloride, aluminium halides and boron halides or carboxylic acids, especially trifluoroacetic acid, as well as the catalysts named in the initially mentioned British Pat. Specification 880,022.

The polyols of the formula III are known compounds and the following may be mentioned as diols: ethylene glycol, porpane-1,3-diol, propane-1,2-diol, neopentylglycol, butane-1,4-diol, hexane-1,6-diol, 2,2-diethyl-propane-1,3-diol, 2-methyl-2-propylpropane-1,3-diol, 2,2,4- and 2,4,4-trimethylhexane-1,6-diol, 2-methyl-2-ethylpropane-1,3-diol, octane-1,8-diol, hydroxypivalic acid neopentylglycol ester, 1,1-, 1,2-, 1,3- and 1,4-bis-(hydroxymethyl)-cyclohexane and the corresponding unsaturated cyclohexene derivatives, such as 1,1-bis-(hydroxymethyl)-cyclohexene, 1,4-bis-(hydroxymethyl)-cyclohexane, 1,4-bis-(hydroxymethyl)-benzene, bis-oxyethylated bisphenol A, bis-oxyethylated hydroquinone and the addition products obtained by addition reaction of 2 mols of alkylene oxide, especially ethylene oxide, with 1 mol of any desired diol or with mononuclear or polynuclear N-heterocyclic compounds, such as hydantoin and its derivatives, dihydrouracil and its derivatives, barbituric acid and its derivatives, benzimidazolone or tetrahydrobenzimidazolone and their derivatives, bis-hydantoin and bis-dihydrouracil and their derivatives. The following may be mentions as examples of such compounds: 1,3-di-(β-hydroxyethyl)-5,5-dimethylhydantoin, 1,3-di-(β-hydroxyethyl)-5-isopropylhydantoin, 1,3-di-(β-hydroxyethyl)-benzimidazolone, 1,3-di-(β-hydroxyethyl)-tetrahydrobenzimidazolone and 1,1'-methylene-bis-(3-β-hydroxyethyl-5,5-dimethylhydantoin).

The following are examples of compounds which can be employed as triols of the formula III: 1,1,1-tri-(hydroxymethyl)-ethane, 1,1,1-tri-(hydroxymethyl)-propane, tri-(hydroxymethyl)-nitromethane, glycerol, hexane-1,2,6-triol, butane-1,2,4-triol and the addition products obtained by addition reaction of 1–3 mols of alkylene oxide, especially ethylene oxide, with these triols. Pentaerythritol is preferably used as a tetrahydric alcohol.

The polysiloxanes, possessing reactive groups, of the formula IV are known compounds. For example, the polysiloxanes, containing hydroxyl groups, of the formula IV can be manufactured in accordance with the process described in French Pat. No. 950,582 by hydrolysing dialkyldichlorosilanes and/or diphenyldichlorosilanes in sulphuric acid. A summarising description of further processes for the manufacture of the polysiloxanes of the formula IV is given by W. Noll in "Chemie und Technologie der Silicone" ("Chemistry and Technology of the Silicones"), Verlag Chemie GmbH, 1968, on pages 162–206.

Examples which may be mentioned of polysiloxanes, containing alkoxy groups or acyloxy groups, of the formula VI are the polydimethylsiloxanes, polymethylpropylsiloxanes, polymethylphenylsiloxanes and polyphenylsiloxanes having methoxy, ethoxy and acetoxy end groups. The average molecular weight of these polysiloxanes is in the range from 300 to 3,000, preferably 500 to 2,500.

As diols of the formula VI it is possible to use the same di-primary diols mentioned under formula III, and also di-secondary diols, such as, for example, 2,2-bis-(4-hydroxycyclohexyl)-propane and the addition products obtained by addition reaction of 2 mols or propylene oxide, butylene oxide or styrene oxide with any desired diols or with the abovementioned N-heterocyclic compounds.

The diols of the formula VI which are used are preferably those which contain a primary and a secondary hydroxyl group in the molecule, such as, for example, propane-1,2-diol, butane-1,3-diol, 2,2-dimethylhexane-1,3-diol, 2,2,4-trimethylpentane-1,3-diol and 2-ethylhexane-1,3-diol.

The polysiloxanols according to the invention can be used for the manufacture and modification of organic resins, such as urethane resins or epoxide resins and give flexible, hydrophobic plastics having valuable mechanical properties. The polysiloxanols according to the invention are colourless to slightly coloured liquids and, compared to conventional polysiloxanes, have better compatibility with curable mixtures consisting of polyepoxides and polycarboxylic acid anhydrides, that is to say are more easily processible with these. The new polysiloxanols are also valuable agents for imparting hydrophobic properties to epoxide resins plasticised with polyesters. It is known that plasticised epoxide resins frequently suffer from the disadvantage that with increasing plasticisation the moulded materials manufactured from these resins tend to show increased water absorption. Thus, for example, the water absorption of the moulded materials manufactured from plasticised epoxide resins modified with polysiloxanediols is extremely low even after several hours in boiling water.

The polysiloxanols according to the invention can be processed together with curable mixtures, consisting of epoxide resins and polycarboxylic acids or polycarboxylic acid anhydrides, in accordance with all known processes. If desired, the curing can also be carried out in two stages by first prematurely discontinuing the curing reaction, which gives a curable precondensate which is still fusible and soluble (a so-called "B-stage"). It is also possible to modify epoxide resins by reacting the polysiloxanol according to the invention with a polycarboxylic acid or a polycarboxylic acid anhydride to give a pre-adduct containing carboxyl groups and then using this for curing or modifying epoxide resins. All polyepoxides, polycarboxylic acids and polycarboxylic acid anhydrides are suitable for this purpose.

EXAMPLE 1

134 g (1.0 mol) of trimethylolpropane, 1,830 g (3.0 mols) of a polymethyl-phenyl-siloxane containing methoxy end groups and having a molecular weight of 610 and 438 g (3.0 mols) of 2-ethyl-hexane-1,3-diol are mixed. This produces a turbid emulsion which on heating becomes homogeneous at about 85°C. The reaction mixture is then allowed to react for 5 hours at 150°C and 3 hours at 170°C/15 mm Hg, until no further distillate is detectable. In the course thereof, 186.7 g of methanol are distilled off. The product is a relatively colourless liquid having a hydroxyl equivalent weight of 611 (theory: 737).

Elementary analysis and the nuclear magnetic resonance spectrum confirm that the product obtained consists of polymethylphenylsiloxanetriol.

EXAMPLE 2

204.0 g (1.0 mol) of hydroxypivalic acid neopentylglycol ester, 1,220 g (2.0 mols) of a plymethyl-phenyl-siloxane containing methoxy end groups and having a molecular weight of 610 and 292 g (2.0 mols) of 2-ethylhexane-1,3-diol are mixed in a sulphonation flask fitted with a descending condenser. This produces a turbid emulsion which on warming becomes homogeneous at 90°C. The reaction mixture is then heated further to 160°–180°C under nitrogen, in the course of which the elimination and distillation of the methanol starts. The reaction slows up in the course of time and is complete after approx. 7 hours. To complete the reaction and to remove the last remnants of methanol, the reaction is continued for a further 3 hours at 150°C and 25 mm Hg. According to a gas chromatogram, this also removes low molecular by-products of the siloxane, in addition to small amounts of unconverted glycols.

The product obtained is a colourless liquid of low viscosity and has a hydroxyl equivalent weight of 569.

EXAMPLE 3

58.8 g (0.2 mol) of a trihydroxy compound manufactured by addition reaction of 3 mols of propylene oxide with 1 mol of glycerol, the manufacture of the compound being described in more detail below, are mixed with 408 g (0.6 mol) of a linear polymethyl-phenyl-siloxane having methoxy end groups and a molecular weight of 680 and the mixture is heated to 180°C under a nitrogen atmosphere. The reaction mixture, which consists of two phases at room temperature, becomes homogeneous at 110°C and then eliminates methanol. After 4½ hours, the elimination of methanol subsides, after which 92.0 g (0.6 mol) of 2-ethylhexane-1,3-diol are added. The reaction is then continued for a further 7 hours at 180°C and is finally continued for 1 hour at 180°C/15 mm Hg to remove all low-boiling components. The product is a pale yellowish viscous oil and has a hydroxyl equivalent weight of 1,529.

ADDITION REACTION OF PROPYLENE OXIDE WITH GLYCEROL 2.0 ml of boron trifluoride etherate are added cautiously to 276 g (3 mols) of glycerol. The dropwise addition of 522 g (9 mols) of propylene oxide, whilst stirring, is then started. The temperature in the reaction mixture should initially be 25°C and should be raised by the exothermic reaction which occurs. A reaction temperature of 33°–35°C is maintained by external cooling with ice and sodium chloride whilst continuing the dropwise addition of propylene oxide. The duration of the total addition is under these conditions approx. 160 minutes. Towards the end of the addition, only a slight exothermic reaction remains noticeable. The mixture is then stirred for a further hour at 40°C. To remove the catalyst, 300 ml of methanol and 31 cm$^3$ of freshly pretreated strongly basic ion exchanger are added, the mixture is stirred overnight at 40°C, the ion exchanger is then again filtered off and the reaction mixture is concentrated. The colourless, slightly viscous product has a hydroxyl equivalent weight of 98 (theory 89).

USE EXAMPLES

EXAMPLE I 70 parts by weight of the polyol, containing polysiloxane groups, manufactured according to Example 1 are mixed with 100 parts by weight of an adduct containing epoxide groups, the manufacture of which is described below, 35 parts by weight of hexahydrophthalic anhydride, 10 parts by weight of an acid adduct curing agent, the manufacture of which is also described below, and 1 part by weight of a solution of 0.82 part by weight of sodium in 100 parts by weight of 2,4-dihydroxy-3-hydroxymethylpentane with addition of 300 parts by weight or quartz powder (16,900 mesh) at 120°C, and the mixture if poured into an aluminium mould warmed to 120°C and cured for 6 hours at this temperature.

The resulting castings are very flexible and strongly hydrophobic and have the following properties:

| | | |
|---|---|---|
| Resistance to hydrolysis by water at 100°C | | up to 100 hours |
| Water absorption | at 20°C after 20 days | 0.56% |
| (test specimen | at 20°C after 100 days | 0.78% |
| 60 × 10 × 4 mm) | at 100°C after 1 hour | 0.29% |
| | at 100°C after 75 hours | 0.70% |

MANUFACTURE OF THE ADDUCT CONTAINING EPOXIDE GROUPS 3,300 g of an acid polyester obtained from 11 mols of sebacid acid and 10 mols of hexanediol and having an acid equivalent weight of 1,530 are allowed to react with 794 g of 3-(3',4'-epoxycyclohexyl)-8,9-epoxy-2,4-dioxaspiro(5.5)undecane having an epoxide content of 6.8 equivalents/kg (corresponding to a ratio of 1 carboxyl group of the polyester: 2.5 equivalents of epoxide group) for 3 hours at 140°C under a nitrogen atmosphere.

MANUFACTURE OF THE ACID ADDUCT CURING AGENT 30 g of hexahydrophthalic anhydride, 50 g of an oligomeric fatty acid mixture manufactured by dimerisation of unsaturated higher fatty acids and having an acid equivalent weight of 292, and 7.5 g of butane-1,4-diol diglycidyl ether are heated for 6 hours at 140°C. 30 g of dodecenylsuccinic anhydride are added to 70 g of the adduct obtained.

EXAMPLE II 80 parts by weight of the polyol, containing polysiloxane groups, manufactured according to Example 1 are mixed with 100 parts by weight of the adduct, containing epoxide groups, described in Use Example I, 35 parts by weight of hexahydrophthalic anhydride, 10 parts by weight of the acid adduct curing agent described in Use Example I and 1 part by weight of a solution of 0.82 part by weight of sodium in 100 parts by weight of 2,4-dihydroxy-3-hydroxymethylpentane, with addition of 300 parts by weight of quartz powder (16,900 mesh) at 120°C, and the mixture is poured into an aluminium mould warmed to 120°C and is cured for 6 hours at this temperature.

The resulting castings are very flexible and strongly hydrophobic and have the following properties:

| Resistance to hydrolysis by water at 100°C | | up to 90 hours |
|---|---|---|
| Water absorption | at 20°C after 20 days | 0.49% |
| (test specimen | at 20°C after 100 days | 0.71% |
| 60 × 10 × 4 mm) | at 100°C after 1 hour | 0.27% |
| | at 100°C after 75 hours | 0.47% |

EXAMPLE III 90 parts by weight of the polyol, containing polysiloxane groups, manufactured according to Example 2 are mixed with 100 parts by weight of the adduct, containing epoxide groups, described in Use Example I, 15 parts by weight of hexahydrophthalic anhydride, 35 parts by weight of the acid adduct curing agent described in Use Example I and 1 part by weight of a solution of 0.82 part by weight of sodium in 100 parts by weight of 2,4-dihydroxy-3-hydroxymethylpentane, with addition of 300 parts by weight of quartz powder (16,900 mesh) at 120°C, and the mixture is poured into an aluminium mould warmed to 120°C and is cured for 6 hours at this temperature.

The resulting castings are very flexible and strongly hydrophobic and have the following properties:

| Resistance to hydrolysis by water at 100°C | | up to 40 hours |
|---|---|---|
| Water absorption | at 20°C after 20 days | 0.42% |
| (test specimen | at 20°C after 100 days | 0.65% |
| 60 × 10 × 4 mm) | at 100°C after 1 hour | 0.25% |
| | at 100°C after 10 hours | 0.34% |

COMPARISON EXAMPLE

Instead of a polyol containing polysiloxane groups, 88 parts by weight of a polyester containing hydroxyl end groups, manufactured by reaction of 7 mols of adipic acid, 4 mols of neopentylglycol and 4 mols of butane-1,4-diol at 165°C, until and hydroxyl equivalent weight is between 800 and 900, are mixed with 100 parts by weight of the adduct, containing epoxide groups, described in Use Example I, 35 parts by weight of hexahydrophthalic anhydride, 10 parts by weight of the acid adduct curing agent described in Use Example I and 1 part by weight of a solution of 0.82 part by weight of sodium in 100 parts by weight of 2,4-dihydroxy-3-hydroxymethylpentane, with addition of 300 parts by weight of quartz powder (16,900 mesh) at 120°C and the mixture is poured into an aluminium mould warmed to 120°C and is cured for 6 hours at this temperature.

The resulting castings are very flexible and have the following properties:

| Water absorption | at 20°C after 20 days | 1.04% |
|---|---|---|
| (test specimen | at 20°C after 100 days | 1.97% |
| 60 × 10 × 4 mm) | at 100°C after 1 hour | 0.81% |
| | at 100°C after 75 hours | dissolves |

EXAMPLE IV 90 parts by weight of the triol, containing polysiloxane groups, manufactured according to Example 3 are mixed with 100 parts by weight of 3',4'-epoxycyclohexylmethyl-3,4-epoxycyclohexyl carboxylate having an epoxide content of 7.3 equivalents/kg, 46 parts by weight of hexahydrophthalic anhydride, 1.5 parts by weight of butanediol diglycidyl ether, 7.5 parts by weight of dodecenylsuccinic anhydride, 70 parts by weight of an oligomeric fatty acid mixture manufactured by dimerisation of unsaturated higher fatty acids and having an acid equivalent weight of 292 and 1 part by weight of a solution of 0.82 part by weight of sodium in 100 parts by weight of 2,4-dihydroxy-3-hydroxymethylpentane as the catalyst, with addition of 400 parts by weight of quartz powder (K 8) as the filler, at 120°C, and the mixture is poured into an aluminium mould warmed to 120°C and is cured for 10 hours at this temperature.

The resulting casting have the following properties:

| Water absorption after 100 hours at 100°C | 2.4% |
|---|---|
| Water absorption after 200 hours at 100°C | 3.7% |

We claim:
1. A polysiloxane of formula I

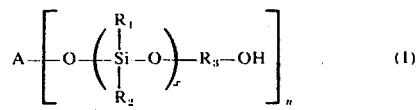

wherein A denotes a di- or three-valent aliphatic or cycloaliphatic-aliphatic residue with 2–15 C atoms in the molecule, $R_1$ and $R_2$ each denote a methyl, ethyl, propyl or phenyl, and wherein $R_1$ and $R_2$ on the same Si atom denote identical substituents and within the siloxane chain denote different substituents, $R_3$ denotes an alkylene with 2–6 C atoms, a lower alkyl-substituted alkylene with 2–6 C atoms in the alkylene chain, or a cycloaliphatic-aliphatic residue, n denotes the number 2 or 3 and x denotes a number from 2 to 20.

2. A polysiloxane according to claim 1, wherein in the formula II

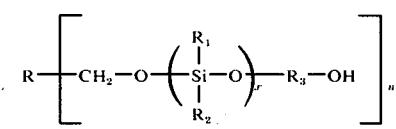
(II)

R denotes a di- or three-valent aliphatic or cycloaliphatic-aliphatic residue with 2–10 C atoms in the molecule, $R_1$ and $R_2$ each denote a methyl, ethyl, propyl or phenyl, and whereby $R_1$ and $R_2$ on the same Si atom denote identical substituents and within the poly-siloxane chain denote differennt substituents, $R_3$ denotes an alkylene radical with 2–6 C atoms, a lower alkyl-substituted alkylene with 2–6 C atoms in the alkylene chain or a cycloaliphatic-aliphatic radical, n denotes the number 2 or 3 and x denotes a number from 2 to 20.

3. A polysiloxane according to claim 2, characterised in that in the linear polysiloxane chain dimethylsiloxane units alternate with dipropylsiloxane or diphenylsiloxane units and $R_3$ denotes a lower alkyl-substituted alkylene with 2 to 3 C atoms in the alkylene chain, obtained by removal of the primary and secondary hydroxyl group.

4. A polysiloxane according to claim 3, characterised in that $R_3$ denotes the 2-ethyl-3-propylpropylene residue.

5. A polysiloxane according to claim 1 wherein A is the aliphatic residue from trimethylolpropane, $R_1$ and $R_2$ are each methyl on one silicon atom and are each phenyl on the alternate silicon atom in the polysiloxane chain, $R_3$ denotes 2-ethyl-3-propylpropylene, n denotes 3, and x denotes 2.

* * * * *